(12) United States Patent
Jamieson et al.

(10) Patent No.: US 7,771,760 B2
(45) Date of Patent: Aug. 10, 2010

(54) OILS OF CAPSAICINOIDS AND METHODS OF MAKING AND USING THE SAME

(75) Inventors: Gene Curtis Jamieson, Boulder Creek, CA (US); Naweed Muhammad, Fremont, CA (US); Keith R. Bley, Mountain View, CA (US)

(73) Assignee: NeurogesX, Inc., San Carlos, CA (US)

( * ) Notice: Subject to any disclaimer, the term of this patent is extended or adjusted under 35 U.S.C. 154(b) by 157 days.

(21) Appl. No.: 11/394,495

(22) Filed: Mar. 31, 2006

(65) Prior Publication Data

US 2006/0233901 A1 Oct. 19, 2006

Related U.S. Application Data

(60) Provisional application No. 60/667,546, filed on Apr. 1, 2005.

(51) Int. Cl.
*A61K 36/81* (2006.01)
(52) U.S. Cl. .................................................. 424/760
(58) Field of Classification Search ................... None
See application file for complete search history.

(56) References Cited

U.S. PATENT DOCUMENTS

| | | | |
|---|---|---|---|
| 4,387,107 A | 6/1983 | Klein et al. | |
| 4,424,205 A | 1/1984 | LaHann et al. | |
| 4,493,848 A | 1/1985 | LaHann et al. | |
| 4,599,379 A | 7/1986 | Flesher et al. | |
| 4,628,078 A | 12/1986 | Glover et al. | |
| 4,812,446 A | 3/1989 | Brand | |
| 4,835,206 A | 5/1989 | Farrar et al. | |
| 4,849,484 A | 7/1989 | Heard | |
| 4,911,933 A | 3/1990 | Gilbard | |
| 5,100,660 A | 3/1992 | Hawe et al. | |
| 5,288,814 A | 2/1994 | Long, II et al. | |
| 5,290,816 A | 3/1994 | Blumberg | |
| 5,468,814 A | 11/1995 | Stover et al. | |
| 5,523,017 A | 6/1996 | Moran et al. | |
| 5,698,191 A | 12/1997 | Wiersma et al. | |
| 5,747,052 A | 5/1998 | Mimikos et al. | |
| 5,827,886 A | 10/1998 | Hersh | |
| 5,856,361 A | 1/1999 | Holt et al. | |
| 5,910,512 A | 6/1999 | Conant | |
| 5,922,331 A | 7/1999 | Mausner | |
| 5,962,532 A | 10/1999 | Campbell et al. | |
| 5,994,407 A | 11/1999 | Cuilty-Siller | |
| 6,013,270 A | 1/2000 | Hargraves et al. | |
| 6,015,763 A | 1/2000 | Vlasblom | |
| 6,113,892 A | 9/2000 | Newell et al. | |
| 6,133,212 A | 10/2000 | Elliott et al. | |
| 6,203,804 B1 | 3/2001 | Murakado et al. | |
| 6,239,180 B1 | 5/2001 | Robbins | |
| 6,248,788 B1 | 6/2001 | Robbins et al. | |
| 6,277,385 B1 | 8/2001 | Luke | |
| 6,348,502 B1 * | 2/2002 | Gardiner et al. | 514/627 |
| 6,390,291 B1 | 5/2002 | Garrill et al. | |
| 6,403,589 B1 | 6/2002 | Meert et al. | |
| 6,428,772 B1 | 8/2002 | Singh et al. | |
| 6,569,463 B2 | 5/2003 | Patel et al. | |
| 6,593,370 B2 | 7/2003 | Tamura et al. | |
| 6,641,825 B2 | 11/2003 | Scholz et al. | |
| 2001/0002406 A1 | 5/2001 | Robbins | |
| 2004/0126430 A1 | 7/2004 | Angel et al. | |
| 2004/0180081 A1 | 9/2004 | Angel et al. | |

FOREIGN PATENT DOCUMENTS

| | | |
|---|---|---|
| EP | 0 228 868 A2 | 7/1987 |
| EP | 0 228 868 A3 | 7/1987 |
| FR | 2 721 213 A1 | 9/1996 |
| FR | 2 721 213 B1 | 9/1996 |
| WO | WO-02/102398 A1 | 12/2002 |
| WO | WO-2004/021990 A2 | 3/2004 |
| WO | WO-2004/021990 A3 | 3/2004 |
| WO | WO-2005/027642 A1 | 3/2005 |

OTHER PUBLICATIONS

Allen, L.V. (Nov. 1998). "Coumarin: Agent With Many Uses," *U.S. Pharm.* 23:106-108.
Amjad, Z. et al. (May 1992). "Carbomer Resins: Past, Present and Future," *Cosmetics & Toiletries* 107(5):81-85.
Anonymous. (2000). Capsaicin Data Sheet located at <http://wholehealthmd.com/ME2/Apps/AWHN/Modules/Drugs/Printasp?id=F2D48C90D57346DFB35E2...>, last visited Aug. 30, 2006, 4 pages.
British Industrial Biological Research Association. (1991). "Toxicity Profile: Polyethylene Glycol 300 (PEG 300)," *British Industrial Biological Research Association Government Reports Announcements and Index* 19:1-5.
Brown, V.K.H. et al. (Jan. 1975). "Decontamination Procedures for Skin Exposed to Phenolic Substances," *Arch. Environ Health* 30:1-6.
Büyükafsar, K. et al. (2003). "Isolated Perfused Rabbit Ear Model for the Assessment of Transdermal Drug Delivery," *Kocatepe Tip Dergisi* 1:29-37.
Edlich, R.F. et al. (Nov. 6, 2003). "Burns, Chemical" located at <http://www.emedicine.com/plastic/topic492.html>, last visited on Jul. 6, 2004, 17 pages.

(Continued)

*Primary Examiner*—Christopher R. Tate
(74) *Attorney, Agent, or Firm*—Morrison & Foerster LLP

(57) ABSTRACT

Oils of capsaicinoids and methods of making and using them are described. In some variations, the oils of capsaicinoids comprise at least 40% w/w capsaicinoid and a solvent capable of solubilizing the capsaicinoid, wherein the oil of capsaicinoid is substantially free of capsaicinoid crystals or capsaicinoid precipitates. In other variations, the oils of capsaicinoids consist essentially of at least 40% w/w capsaicinoid and a solvent capable of solubilizing the capsaicinoid. The solvent may be a semi-volatile solvent, a non-volatile solvent, or a volatile solvent, and the oil may comprise at least 50% w/w capsaicinoid, 60% w/w capsaicinoid, 70% w/w capsaicinoid, 80% w/w capsaicinoid, 90% w/w capsaicinoid, or 95% w/w capsaicinoid. The oil of capsaicinoid may also include a crystallization inhibitor.

26 Claims, No Drawings

OTHER PUBLICATIONS

Govindarajan, V.S. et al. (1991). "Capsicum—Production, Technology, Chemistry, and Quality. Part V. Impact on Physiology, Pharmacology, Nutrition, and Metabolism; Structure, Pungency, Pain, and Desensitization Sequences," *Food Science and Nutrition* 29(6):435-474.

Hemker, W. (Nov. 1991). "Universal Oil-in-Water Polyelectrolyte Emulsifiers for Advanced Cosmetic Product Formulation," *Parfümerie und Kosmetik.* 72(Nov. 1991):730-741.

International Search Report mailed on Jun. 30, 2004, for PCT Patent Application No. PCT/US03/27742 filed on Sep. 5, 2003, 3 pages.

Jensen, P.G. et al. (2003). "Field Evaluation of Capsaicin as a Rodent Aversion Agent for Poultry Feed," *Pest Manag. Sci.* 59(8):1007-1015.

Jordt, S-E. et al. (Feb. 8, 2002). "Molecular Basis for Species-Specific Sensitivity to "Hot" Chili Peppers," *Cell* 108(3):421-430.

Laws, R. et al. (Nov. 12, 2002). "Burns, Chemical" located at <http://www.emedicine.com/derm/topic777.html>, last visited on Jul. 6, 2004, 14 pages.

Leber, A.P. et al. (1990). "Triethylene Glycol Ethers: Evaluations of In Vitro Absorption Through Human Epidermis, 21-Day Dermal Toxicity in Rabbits, and a Developmental Toxicity Screen in Rats," *J. Am. Coll. Toxicol.* 9(5):507-515.

Lee, D.C. et al. (Jun. 2003). "Magnesium-Aluminum Hydroxide Suspension For The Treatment of Dermal Capsaicin Exposures," *Acad. Emerg. Med.* 10(6):688-690.

Lochhead, R.Y. et al. eds. (1993). "Encyclopedia of Polymers and Thickners," *Cosmetics & Toiletries* 108(5):95-135.

Miller, C.H. (1994). "Inhibition of NNK Mutagenesis and Metabolism by Chemopreventive Phytochemicals (Tobacco, Nitrosamines)," Abstract, *Diss. Abstr. Int. (B)* 55(6):2219.

Monsereenusorn, Y. et al. (Oct. 1982). "Capsaicin—A Literature Study," *Crit. Rev. Toxicol.* 10(1):321-339.

Olson, C.T. et al. (1991). "Evaluation of Compounds as Barriers to Dermal Penetration of Organophosphates Using Acetylcholinesterase Inhibition," *Toxicology Letters* 55:325-334.

Osol, A. et al. eds. (1975). *Remington's Pharmaceutical Sciences*, 15th Edition, Mack Publishing Co.: Easton, PA, p. xi (Table of Contents Only.).

Pullin, T.G. et al. (1978). "Decontamination of the Skin of Swine Following Phenol Exposure: A Comparison of the Relative Efficacy of Water Versus Polyethylene Glycol/Industrial Methylated Spirits," *Toxicology and Applied Pharmacology* 43:199-206.

Roberts, M.S. et al. (1977). "Permeability of Human Epidermis to Phenolic Compounds," *J. Pharm. Pharmacol.* 29:677-683.

Roberts, M.S. et al. (1978). "The Percutaneous Absorption of Phenolic Compounds: The Mechanism of Diffusion Across the Stratum Corneum," *J. Pharm. Pharmacol.* 30:486-490.

Rumsfield, J.A. et al. (Apr. 1991). "Topical Capsaicin in Dermatologic and Peripheral Pain Disorders," *DICP* 25(4):381-387.

Toh, C.C. et al. (1955). "The Pharmacological Actions of Capsaicin and Analogues," *Brit. J. Pharmacol.* 10:175-182.

United States Pharmacopeial Convention, Inc. eds. (1999). "USP24/NF19 U.S. Pharmcopeia/National Formulary," *United States Pharmacopeial Convention, Inc. Meeting*, Washington, DC, (Mar. 9 -12, 1995) p. 2405.

Watson, H.R. et al. (1978). "New Compounds with the Menthol Cooling Effect," *J. Soc. Cosmet. Chem.* 29:185-200.

Wenninger, J.A. et al. eds. (1997). *International Cosmetic Ingredient Dictionary and Handbook*, Seventh Edition, The Cosmetic, Toiletry, and Fragrance Association: Washington, DC, vol. 1-3, 9 pages (Table of Contents Only.).

Wenninger, J.A. et al. eds. (2000). *International Cosmetic Ingredient Dictionary and Handbook*, Eighth Edition, The Cosmetic, Toiletry, and Fragrance Association: Washington, DC, vol. 1-3, 9 pages(Table of Contents Only.).

Xu, Q. et al. (2005). "Assessment of Antifouling Effectiveness of Two Natural Product Antifoulants by Attachment Study with Freshwater Bacteria," *Environ. Sci. Pollut. Res. Int.* 12(5):278-284.

Xu, Q. et al. (2005). "Evaluation of Toxicity of Capsaicin and Zosteric Acid and Their Potential Application as Antifoulants," *Environ. Toxicol.* 20(5):467-474.

Zatz, J.L. et al. (Sep.-Oct. 1983). "Evaluation of Solvent-Skin Interaction in Percutaneous Absorption," *J. Soc. Cosmet. Chem.* 34:327-334.

* cited by examiner

OILS OF CAPSAICINOIDS AND METHODS OF MAKING AND USING THE SAME

RELATED APPLICATIONS

This application claims priority to U.S. Provisional Application Ser. No. 60/667,546, filed Apr. 1, 2005, which is hereby incorporated by reference in its entirety.

FIELD

The oils of capsaicinoids described here and methods of making and using them are in the field of dermal drug delivery for the treatment of pain.

BACKGROUND

In capsaicinoid molecules an aromatic ring is attached, generally through an amide functional group, to an aliphatic long chain. These molecules exist as solids. Because the solid physical state is not optimum for effective penetration into the skin, dermal formulations of capsaicinoids are either liquids, gels, or patches, whereby capsaicinoids have been solubilized and the resulting solution accordingly adapted to the nature of the dosage form. In dermal dosage forms, penetration enhancers are generally used to facilitate/enhance penetration of a capsaicinoid into the skin. The presence of an aliphatic chain in capsaicinoid molecules gives them an intrinsic ability to penetrate tissues such as skin or mucous membranes. However, the intrinsic ability of capsaicinoids to penetrate into the skin is impeded by the lack of thermodynamic activity when in solid form. A change of state from solid to liquid greatly enhances thermodynamic activity. Also, some of the formulation ingredients such as adhesives impede capsaicinoids' ability to diffuse out of the formulation and hence penetrate into the skin. This invention eliminates the necessity to include such ingredients (e.g., penetration enhancers or adhesives) and utilizes the intrinsic ability of capsaicinoids to penetrate skin much more effectively when compared to their solid state.

With the addition of every single ingredient to any formulation the level of concern rises with respect to physicochemical, pharmacological, and toxicological properties of the formulation. These concerns promote an inclination to keep the system as simple as possible. However, this high level of simplicity is not always attainable due to necessity to meet other performance requirements. Formulation of a capsaicinoid oil would eliminate the necessity to use penetration enhancers as it allows reliance on the intrinsic property of the capsaicinoid to penetrate the skin by simply changing its physical state.

Accordingly, it would be desirable to have new pharmaceutical dosage forms for the treatment of pain that include oils of capsaicinoids.

SUMMARY

Described here is the surprising finding that high purity capsaicinoids, which normally exist as a solid, can be stabilized as an oil. The capsaicinoid oils generally include at least about 40% w/w capsaicinoid and a solvent for solubilizing the capsaicinoid. The capsaicinoid oil is formed such that it is substantially free of capsaicinoid crystals or capsaicinoid precipitates. In one variation, crystallization of the capsaicinoid is prevented by inclusion of a crystallization inhibitor in the oil. In some instances, the solvent itself is a capsaicinoid crystallization inhibitor.

Methods for producing capsaicinoid oils are also described, as well as characterization of the resulting product. The formulation of the substance as an oil has the potential advantage of enhancing delivery when used as a medicine, especially when it is applied topically. Capsaicinoids have certain intrinsic permeation properties but, are typically formulated with other penetration enhancers and formulation aids to ensure that these are presented in a solubilized or liquefied form. Further described here is how the intrinsic permeation properties of capsaicinoids, when presented as an oil, would eliminate the need to co-formulate a capsaicinoid with other penetration enhancers.

DETAILED DESCRIPTION

The capsaicinoid oils described herein are generally formulated to include at least about 40% w/w capsaicinoid and a solvent for solubilizing the capsaicinoid. Immediately after formulation, the oils are substantially free of capsaicinoid crystals or capsaicinoid precipitates. The oils may be inspected, e.g., visually inspected using a microscope, to determine if crystals or precipitates are present.

Methods of Making Oils of Capsaicinoids. As a way of example, and not limitation, we have produced oils of pure synthetic capsaicin by various methods, which yielded a clear liquid, substantially free of capsaicin crystals or precipitates (e.g., greater than 90% free of capsaicin crystals or precipitates, greater than 95% free of capsaicin crystals or precipitates, etc.), and having capsaicin concentrations ranging from >40% to 95% w/w. These clear liquid compositions remained stable for at least two weeks since their preparation, at temperatures ranging from −20° C., 2 to 8° C. and 25° C. The methods used to produce highly concentrated capsaicin oils are similar to the techniques used to make simple solutions, co-solvent solutions, solutions with crystallization inhibitors, and eutectic mixtures, which are well known in the art. For example, the addition of crystallization inhibitors to simple solutions provides a way to increase the capsaicin concentration above the saturation limit of the solvent system alone. Such a combination results in a liquid that will not crystallize or produce precipitates in a manner experienced by simple solutions alone.

Methods used to demonstrate formation of an oil included visual and microscopic examination, and short term physical stability using temperature stressing to induce precipitation and/or crystallization. Other methods that have been employed to assess both stability and formation of oils include: clarity measured by visual means or turbidity, immiscibility with water, viscosity, density and rheological flow characteristics.

In another aspect, an oil of a capsaicinoid is formed in situ upon administration. For example, pure synthetic capsaicin is dissolved in a volatile solvent system such as ethanol. Crystallization inhibitors are added and the resulting formulation is a clear liquid free of precipitate or crystallized capsaicinoid. Upon administration, the more volatile solvent would evaporate leaving a residue of highly concentrated capsaicinoid. Typically, the loss of solvent would leave a solid residue with the result that skin permeation of the solid residue would be minimal. However, with the addition of a crystallization inhibitor, a residual oily film of capsaicin is left on the surface. The combination of the shunt effect given by the volatile solvent system and the in situ generated oil may result in a much greater permeation rate than a similar formulation without the addition of one or more crystallization inhibitors.

In some variations, the oil of a capsaicinoid comprises at least 40% w/w capsaicinoid. In other variations, the oil of capsaicinoid comprises at least 60% w/w capsaicinoid, at least 70% w/w capsaicinoid, at least 80% w/w capsaicinoid, or at least 95% w/w capsaicinoid or at least 99.5% w/w capsaicinoid.

In still other variations, the oils of capsaicinoids described here consist essentially of at least 40% w/w capsaicinoid and a solvent capable of solubilizing the capsaicinoid. These oils may further include a capsaicinoid crystallization inhibitor, for example, polyvinylpyrrolidone. In other variations, the solvent is a capsaicinoid crystallization inhibitor.

Oils of Capsaicinoids. Oils of capsaicinoids produced using the methods described above are clear liquids with a color ranging from water-white to amber brown. The oils are not miscible with water, and have a viscosity similar to long chain alkanols such as oleyl alcohol as determined by visual comparison.

The oils will typically be formed to include capsaicin as the capsaicinoid, but other suitable capsaicinoids may be used. Capsaicin has been used as a penetration enhancer for transdermal delivery of active pharmaceutical ingredients (see Kansa Büyükasar et. al. *Kocatepe Tip Dergisi* (2003), 1, 29-37). Capsaicin is the principle chemical of the essential oils called oleoresins which are extracted from peppers of the genus *Capsicum*. The natural botanical extract contains a mixture of capsaicinoids. Typically, 80 to 90% of the capsaicinoids are made up of capsaicin (69%) and dihydrocapsaicin (22%). The physical properties of capsaicin (CAS registry number: 404-86-4) are: empirical formula=$C_{18}H_{27}O_3N$, molecular weight=305.4 Daltons, white crystalline particles, sparingly soluble in cold water but soluble in benzene, alcohol, ketone, ether and paraffin oils (Monsereenusom et al., 1982, Rumsfield and West, 1991). The pure drug substance and natural botanical extract are solids occurring as a microcrystalline white powder.

Capsaicin itself is also pharmacologically active and has been used to treat peripheral neuralgias, interstitial cystitis, osteoarthritis, as well as other painful conditions. The intrinsic permeation properties of capsaicin have not been shown in topical formulations (e.g., creams, gels, ointments, or salves) and typically, the presence of other inactive ingredients in these formulations affect permeation properties of the capsaicin. A surprising finding is that capsaicin may be converted to and stabilized in a highly concentrated liquid form by the addition of crystallization inhibitors or retardants such that high purity capsaicin may exist as a liquid suitable for direct topical administration (e.g., as a highly concentrated oil). The advantage is that when presented in a liquid form, intrinsic permeation properties of capsaicin would suffice to attain desired level of dermal drug delivery and pharmacological effect. A new physical form of synthetic or an enriched extract of capsaicin and methods for producing the same are described.

Other suitable capsaicinoids that may be used to formulate an oil include cis-capsaicin, nonivamide, dihydrocapsaicin, homocapsaicin, nordihydrocapsaicin, homodihydrocapsaicin, olvanil, aravanil and analogs of capsaicin such as capsaicin ester and derivatives amide side chain.

We have found that crystallization inhibitors, typically used to prevent fixed oils from crystallizing or used to prevent precipitation of solubilized active pharmaceutical ingredients in dosage forms, may be used to prevent capsaicin from crystallizing. Examples include, but are not limited to, Luvitol® BD 10 P (BASF), povidone and its derivatives; dextrin derivatives, polyethylene glycol, polypropylene glycol, mannitol and glycerin, and mono and diglycerides of essential oils, polyglycerin fatty acid esters, sucrose palmitic acid ester, pentaerythritol ester of wood rosin (Pentalyn A®), and Eudagrits®. Crystallization inhibitors may range from 0.1 to 10% w/w. More preferably 2% or at least 1% and may be formulated as a solution such as a 10% addition of a 10% Kollidon® in PEG 400.

The capsaicinoid oils described here usually include a solvent capable of solubilizing the capsaicinoid. Examples of solvents that may be used include volatile solvents, semi-volatile solvents, and non-volatile solvents.

A. Volatile Solvents

Volatile organic solvents suitable for use in the capsaicinoid oils are low molecular weight compounds in which capsaicin is especially soluble. Examples include methanol, ethanol, acetone, isopropanol, n-propanol, cyclohexane and alkanes with molecular weight less than dodecane (C-12). In the preparation, capsaicinoid is dissolved until the solution is saturated. Crystallization inhibitors such as Kollidon® 17 PF (also known as povidone available from BASF) and co-solvents may be added. The saturated solution is filtered to remove any residual undissolved capsaicinoid. Substantially all of the volatile solvent is removed (e.g., greater than 60%, greater than 70%, greater than 80%, greater than 90%, greater than 95%, etc.) resulting in a subcooled liquid; that is a liquid state of a pure organic compound in which the most stable state at standard conditions is a solid. Without being bound to any particular theory, it is thought that the presence of the crystallization inhibitor prevents homogeneous nucleation by affecting the lattice energy for capsaicin crystallization. An oil of capsaicinoid results.

B. Semi-Volatile Solvents

Semi-volatile solvents that may be used to formulate the capsaicinoid oils include many volatile essential oils such as clove oil, tea tree oil, sesame oil, and cineole. In one variation, the essential oil is a fixed oil, which may also be known as a carrier oil. Other may be used as a suitable semi-volatile solvent. Examples include Transcutol® (Gattefossé, France), Glycofurol®, oleyl alcohol, propylene glycol, monoterpenes, cineole (Sigma-Aldrich Chemical Co, UK), menthol, ethyl oleate, isopropyl myristate, benzyl alcohol, and alkanes or alkanols, alkenols, alkanoic and alkenoic acids from C-12 through C-28. Semi-volatile solvents typically have a boiling point higher than the melting point of the capsaicinoid. Capsaicinoid and crystallization inhibitors are added as a suspension to the medium. The temperature is raised above the melting point of capsaicinoid and below the boiling point of the solvent. Substantially all of the semi-volatile solvent is removed (e.g., greater than 60%, greater than 70%, greater than 80%, greater than 90%, greater than 95%, etc.). As the solution cools, crystallization or precipitation of capsaicinoid is prevented by the presence of the inhibitors resulting in a liquid composition (i.e., an oil). The medium itself may act as a crystallization inhibitor.

C. Non-Volatile Solvents

Non-volatile solvent systems that may be used in the capsaicinoid oils include high concentration capsaicinoid solubilized in polyethylene glycol 400, Lutrol® (polyethylene polyoxypropylene block copolymer available from BASF), glyceryl monooleate, glycerin, lanolin, low melting waxes, sesquiterpenes and alkanes, alkenes, alkanoic and alkenoic acids >C-28. Similar to the semi-volatile preparation, capsaicinoid and crystallization inhibitors are added to the medium as a suspension. The temperature is raised above the melting point of capsaicinoid. As the solution cools, crystallization or precipitation of capsaicinoid is prevented by the presence of the inhibitors resulting in a liquid (i.e., an oil). The medium itself may act as a crystallization inhibitor.

Dosage forms and applications. The oils of capsaicinoid described here may be directly administered as an oil, or may be formulated as a patch, gel, ointment, cream, or lotion, for topical application to tissues such as skin and mucous membrane. The capsaicinoid oils may be topically applied in any of the aforementioned dosage forms for at least about 10 minutes, at least about 30 minutes, or at least about one hour, but is not so limited. The duration of application will vary depending on such factors as dosage form used, type and amount of capsaicinoid included, and the like. Thereafter, the capsaicinoid oil may be removed, e.g., by application of a cleansing gel. Exemplary cleansing gels that may be used are described in commonly owned co-pending application Ser. No. 10/655,911, which is hereby incorporated by reference in its entirety.

For use in a patch product, the liquid form of a capsaicinoid plus crystallization inhibitors may be directly blended in an adhesive mass wherein the liquid capsaicinoid droplet is immiscible with the adhesive. One example is a silicon based adhesive. Such a system is called a microreservoir patch where the drug in adhesive mass is a liquid. Alternately, liquefied capsaicinoid can be adsorbed onto an inert particle such as bentonite or diatomaceous earth and formulated into a drug in adhesive matrix patch design. A traditional liquid reservoir multilayered patch design is also possible.

Emulsions, microemulsions, or other biphasic topical creams, ointments, or gels may also be prepared. Direct emulsification of oil of capsaicinoid may be possible, for example an oil-in-water emulsion wherein the hydrophobic core is largely composed of capsaicinoid oil. Other surfactants or formulary excipients may be added to physically stabilize the emulsion.

The capsaicinoid oils may be included in dosage forms used to treat any capsaicin-responsive condition, such as, but not limited to, peripheral neuropathic pain syndromes, postherpetic neuralgia, painful diabetic neuropathy, trigeminal neuralgia, traumatic neuropathic pain, erythromelalgia, osteoarthritis, rheumatoid arthritis, fibromyalgia, lower back pain, psoriasis, itch, pruritus, cancer, warts, prostatic hypertrophy, hyperpigmentation, wrinkles and viral infections.

Moreover, capsaicinoid oils could have numerous applications in agricultural or commercial activities (e.g., in developing or cultivating various agricultural or commercial products) due to their intrinsic ability to deter or repel rodents or insects or other ambulatory animals, or deter bacteria or maritime creatures from attaching themselves to docks or the hulls of ships. This is due, in part, to the pungency of capsaicin mediated through the TRPV1 receptor, which can be exploited. More specifically, developing techniques for reducing animal feed contamination by rodents and controlling rodent populations is critical to efforts aimed at reducing the occurrence of bacteria infection on poultry farms. Capsaicinoids produce burning sensations in the mouth of mammals and are used effectively as deterrents for some pest species. Applied to poultry feed, capsaicinoid oils may be effective as an aversive agent to deter rodent feeding, but they do no deter birds because the TPRV1 receptor of birds is far less capsaicin-responsive (Jordt S E, Julius D. Molecular basis for species-specific sensitivity to "hot" chili peppers. *Cell.* 2002. 108(3):421-30). Use of capsaicinoid-treated feed on poultry farms may substantially reduce feed contamination by rodents and ultimately the incidence of bacterial infection in poultry. (Jensen P G, Curtis P D, Dunn J A, Austic R E, Richmond M E. Field evaluation of capsaicin as a rodent aversion agent for poultry feed. *Pest Manag Sci.* 2003. 59(9): 1007-15).

In another variation, the capsaicinoid oils may be used as anti-foulants. Anti-foulants deter the attachment of marine organisms (including bacteria) to submerged surfaces such as the piers, docks or the hulls of boats. The most commonly used anti-foulant has been tributyltin (TBT). TBT systems are highly effective but are also toxic to non-target organisms; the use of the TBT-based coatings will be completely banned in the US by Jan. 1, 2008. Therefore, there is an urgent need to seek out suitable non-toxic alternatives. Capsaicinoids are attractive alternatives to the currently used toxic metal-based anti-foulants, as they are far less toxic (Xu Q, Barrios C A, Cutright T, Zhang Newby B M. Evaluation of toxicity of capsaicin and zosteric acid and their potential application as antifoulants. *Environ Toxicol.* 2005, 20(5):467-74.) but still quite effective (Xu Q, Barrios C A, Cutright T, Newby B M. Assessment of antifouling effectiveness of two natural product antifoulants by attachment study with freshwater bacteria. *Environ Sci Pollut Res Int.* 2005. 12(5):278-84). Capsaicinoid oils constitute a particularly convenient means to apply an anti-foulant to maritime structures.

In yet another variation, capsaicin-based products may be used to repel insects (including aphids, spider mites, thrips, leaf miners, whiteflies, lace bugs and leafhoppers) from plants, especially fruits and vegetables; for example, citrus fruits, root and tuber vegetables, bulb vegetables, leafy vegetables, brassica (cole) leafy vegetables, legume vegetables, fruiting vegetables and cucurbit vegetables. With time and standard cleaning procedures, topical capsaicin administration does not affect the taste of produce. Capsaicin-based repellents can also be used on all indoor and outdoor ornamental plants. Accordingly, capsaicinoid oils constitute a particularly convenient means to apply an insect repellent to plants, fruits and vegetables.

EXAMPLES

The following examples serve to more fully describe the manner of making and using the above-described capsaicoid oils. It is understood that these examples in no way serve to limit the scope of this invention, but rather are presented for illustrative purposes.

Furthermore, the following examples will employ, unless otherwise indicated, conventional techniques of pharmaceutical formulation, medicinal chemistry, and the like, which are within the skill of the art. Such techniques are explained fully in the literature. Efforts have been made to ensure accuracy with respect to numbers (e.g., amounts, ratios, etc.), but some experimental error and deviation should be accounted for. Unless indicated otherwise, parts are parts by weight. All components are obtainable commercially unless otherwise indicated.

Example 1

Solubilization with a Volatile Solvent Plus Inhibitor

Capsaicin solutions at the minimum required concentration (40%) were prepared by dissolving the drug in a suitable solvent with or without the addition of a crystallization inhibitor as follows: Capsaicin was weighed into a borosilicate vial followed by the remaining excipients (usual sample size 1 g). The vial was closed and the ingredients were vortex mixed and visually inspected. The formulation was left to stand overnight at room temperature. The experiment was considered successful if a clear liquid was obtained.

Maximum solubility of capsaicin in the selected solvents was determined as follows: To a fixed amount of each solvent (100 mg) a known amount of capsaicin (100 mg) was added. The sample was vortex mixed until all the capsaicin had dissolved (visual assessment). Further aliquots of capsaicin (100 mg) were added to the sample and vortex mixed until maximum solubility was achieved. Maximum possible kinetic solubility of capsaicin in each solvent was determined visually.

High concentration capsaicin solutions were prepared by dissolving capsaicin in the respective solvent at concentrations marginally below (about 5 to 10% w/w) the maximum solubility as determined as set forth above. Capsaicin was weighed into a borosilicate vial followed by the selected solvent. Ingredients were vortex mixed and visually inspected until all the capsaicin was solubilized. The formulation was left to stand overnight, at room temperature, uncovered.

For the preparation of high concentration capsaicin solutions a specific grade of PVP was identified as a suitable crystallization inhibitor. Kollidon® 17 PF meets the requirements of the current harmonized monographs for povidone in Ph. Eur., USP/NF and JPE. Its main applications comprise the use as a solubilizing agent, dispersant and crystallization inhibitor particularly for injections.

Several example compositions were prepared comparing the maximum possible concentration before and after solvent removal. As shown in the Table 1 below, high concentration compositions were successfully obtained.

Results demonstrated that highly concentrated capsaicin solutions can be prepared by dissolution in a volatile solvent in the presence of a crystallization inhibitor than could be obtained by the solvent's capacity alone. Evaporation of the more volatile component of the mixture resulted in a liquid (i.e., an oil) stabilized by the presence of inhibitor(s).

Example 2

Solubilization with a Non-Volatile Solvent

Solutions of this type were prepared by solubilizing capsaicin in the chosen solvent with the addition of the crystallization inhibitor as follows: Capsaicin (Torcan Chemicals LTD, Canada) and Kollidon® (BASF, Germany) were weighed into a borosilicate vial followed by the remaining excipients (usual sample size 1 g). Ingredients were vortex mixed and visually inspected. The vial was weighed and the formulation was placed in a water bath at 70° C. for 1 hour, leaving the vial open. The vial was cooled, closed and weighed again at the end of the hour. The formulation was left to stand overnight at room temperature. The experiment was considered successful if a clear liquid was obtained. Components of the various compositions prepared are shown in Table 2.

TABLE 1

| | Formulation Code | | | | | | | | | |
|---|---|---|---|---|---|---|---|---|---|---|
| | NG26 | | NG27 | | NG28 | | NG29 | | NG30 | |
| Ingredient | Initial | Final | Initial | Final | Initial | Final | Initial | Final | Initial | Final |
| Capsaicin | 44 | 61 | 44 | 61 | 44 | 68 | 44 | 75 | 44 | 73 |
| Isopropyl Alcohol | 44 | 23 | 44 | 23 | 44 | 11 | N.A. | N.A. | N.A. | N.A. |
| PEG 400 (polyethylene glycol) | 11 | 15 | N.A. | N.A. | N.A. | N.A. | 11 | 17 | N.A. | N.A. |
| Propylene Glycol | N.A. | N.A. | 11 | 15 | N.A. | N.A. | N.A. | N.A. | 11 | 18 |
| Ethanol | N.A. | N.A. | N.A. | N.A. | N.A. | N.A. | 44 | 7 | 44 | 8 |
| Benzyl Alcohol | N.A. | N.A. | N.A. | N.A. | 11 | 19 | N.A. | N.A. | N.A. | N.A. |
| Kollidon ® | 1 | 1 | 1 | 1 | 1 | 2 | 1 | 1 | 1 | 1 |

N.A. = not applicable

TABLE 2

| | Formulation Code | | | | | | | | | |
|---|---|---|---|---|---|---|---|---|---|---|
| Ingredient | NG34 | NG35 | NG36 | NG37 | NG38 | NG39 | NG45 | NG48 | NG50 | NG52 |
| Capsaicin | 80 | 80 | 80 | 80 | 80 | 80 | 85 | 50 | 50 | 50 |
| Menthol | 10 | N.A. | N.A. | 10 | N.A. | N.A. | 10 | N.A. | N.A. | N.A. |
| Clove oil | N.A. | 10 | N.A. | N.A. | 10 | N.A. | N.A. | N.A. | N.A. | N.A. |
| Cineole | N.A. | N.A. | 10 | N.A. | N.A. | 10 | N.A. | N.A. | N.A. | N.A. |
| Glycofurol ® | N.A. | N.A. | N.A. | N.A. | N.A. | N.A. | N.A. | 50 | 50 | N.A. |
| Transcutol ® | N.A. | N.A. | N.A. | N.A. | N.A. | N.A. | N.A. | N.A. | N.A. | N.A. |
| Benzyl Alcohol | N.A. | N.A. | N.A. | N.A. | N.A. | N.A. | N.A. | N.A. | N.A. | 50 |
| 10% Kollidon ® in PEG 400 | 10 | 10 | 10 | N.A. | N.A. | N.A. | 5 | N.A. | N.A. | N.A. |
| PEG 400 (polyethylene glycol) | N.A. | N.A. | N.A. | 10 | 10 | 10 | N.A. | N.A. | N.A. | N.A. |

N.A. = not applicable

Results demonstrated that adding capsaicin to a semi-volatile solvent and heating to above the melting point of capsaicin produced stable compositions in some cases with crystallization inhibitors and in some cases where the solvent system acted as an inhibitor.

Example 3

Hot Melts

Capsaicin oils at high concentrations were formulated. Three formulations at 95%, 99% and 100% capsaicin were prepared. Capsaicin was weighed into a borosilicate vial followed by 10% w/w Kollidon® in PEG 400. The vial was closed and placed in a water bath at 70° C. and visually inspected until all the capsaicin had melted and a clear liquid was formed. For the 100% capsaicin oil, pure capsaicin was weighed into a borosilicate vial, sealed, and placed in a water bath at 70° C., until all the capsaicin had melted. The vial was cooled and the formulation was left to stand at room temperature. The behavior upon cooling was observed in order to determine at which temperatures and for which time frame clear oils could be obtained.

Results demonstrated that only the 95% capsaicin plus 5% of a 10% w/w Kollidon® was sufficiently stable. The 99% and 100% capsaicin compositions crystallized within a short time following cooling to room temperature.

Example 4

Short Term Physical Stability Study

A total of 14 formulations from the above categories were tested for their short-term stability at three different temperature conditions. Formulations were selected to include examples from as many different types as possible, including 100% capsaicin as a comparator.

For the short-term physical stability study, formulations were prepared at a sample size of 3-6 g in 25 ml Duran bottles (borosilicate glass) as described above. Three aliquots of each sample were then transferred into small borosilicate vials, sealed and placed at the three selected temperature conditions: 25° C., 2-8° C. and −20° C. The stability time points investigated at these three temperature conditions were: t=0, t=12 h, t=36 h, t=1 week and t=2 weeks. After each time point, the formulations were assessed for any visual changes, particularly the presence of any crystals or particulates as follows: Samples placed for incubation at 25° C., 2-8° C. and −20° C. were removed from the stability cabinet and placed on the bench. Visual assessment was performed immediately upon removal from the incubator and after 1, 2 and 4 h of standing on the bench at room temperature. Afterwards the samples were returned to their respective incubators.

A number of additional formulations were prepared as a back-up and observed for any visual changes over a two week time period, but only at room temperature.

Example 5

Quick Stability Screening Test—Microscopic Evaluation

Accelerated stability of formulations was investigated using a quick crystallization-screening test. The test involved observation of the behavior of thin films of the formulations under the microscope when reverting back to room temperature after having been frozen. For this purpose, a sample of each formulation was spread on a dual cavity microscopic slide and covered using a cover slip. The cover slip was sealed using a lacquer to prevent any evaporation of the solvents from the formulation. The microscope slides were then placed in the freezer at −20° C. for 1 h, removed and observed under the microscope over a 5 min period at 200× magnification. The presence, formation or disappearing of any crystals and/or precipitates was noted over the observation time. All the 14 formulations selected for the short-term stability study described above were additionally evaluated by this microscopic method.

Example 6

Differential Scanning Calorimetry (DSC)

DSC may be employed to obtain some basic information about the physical properties of capsaicin so that highly concentrated oils can be developed. Therefore, when used, a standard DSC analysis was carried out using a DSC 2920 (TA Instruments). The DSC cell was purged with dry nitrogen (60 $cm^3$/min) and the refrigerator cooling system was purged with nitrogen (150 $cm^3$/min). All DSC analyses were performed in aluminum pans that are hermetically sealed by crimping. Three different protocols were followed for carrying out the DSC analysis:
  a. Increase of temperature from 20° C. to 80° C. at a rate of 10° C./min.
  b. Increase of temperature from 20° C. to 100° C. at a rate of 10° C./min followed by a cooling step to −20° C. at a rate of 10° C./min end a second heating step 150° C.
  c. Increase of temperature from 20° C. to 70° C. at a rate of 10° C./min followed by a cooling step to −20° C. at a rate of 10° C./min and a second heating step 100° C.

The transition temperatures were determined by taking the maximum endotherms of the peaks observed on the heating curves. The heating curves were constructed by plotting the heat flow values, which had been normalized using the sample weight (as W/g), against temperature.

All publications, patents, and patent applications cited herein are hereby incorporated by reference in their entirety for all purposes to the same extent as if each individual publication, patent, or patent application were specifically and individually indicated to be so incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit and scope of the appended claims.

What is claimed as new and desired to be protected by Letters Patent of the United States is:

1. A topical oil in unit dosage form comprising:
   at least 40% w/w of a capsaicinoid;
   a solvent capable of solubilizing the capsaicinoid; and
   a capsaicinoid crystallization inhibitor, wherein the oil is stable at room temperature and is substantially free of capsaicinoid crystals or capsaicinoid precipitates.

2. The oil of claim 1 wherein the capsaicinoid crystallization inhibitor is polyvinylpyrrolidone.

3. The oil of claim 1 wherein the solvent has a molecular weight of about 100 to about 300 Daltons and a boiling point above about 69° C.

4. The oil of claim 1 wherein the solvent is a semi-volatile solvent.

5. The oil of claim 4 wherein the solvent is selected from the group consisting of terpenes, tea tree oils, essential oils, and mixtures thereof.

6. The oil of claim 1 wherein the solvent is a non-volatile solvent.

7. The oil of claim 6 wherein the non-volatile solvent is selected from the group consisting of polyethylene glycol, propylene glycol, tetrahydrofurfuryl alcohol polyethyleneglycol ether, diethylene glycol monoethyl ether, benzyl alcohol and mixtures thereof.

8. The oil of claim 1 wherein the solvent is a volatile solvent.

9. The oil of claim 8 wherein the volatile solvent is selected from the group consisting of methanol, ethanol, isopropyl alcohol, and mixtures thereof.

10. The oil of claim 1 wherein the capsaicinoid is capsaicin and wherein the oil comprises at least 50% w/w capsaicin.

11. The oil of claim 1 wherein the capsaicinoid is capsaicin and wherein the oil comprises at least 60% w/w capsaicin.

12. The oil of claim 1 wherein the capsaicinoid is capsaicin and wherein the oil comprises at least 70% w/w capsaicin.

13. The oil of claim 1 wherein the capsaicinoid is capsaicin and wherein the oil comprises at least 80% w/w capsaicin.

14. The oil of claim 1 wherein the capsaicinoid is capsaicin and wherein the oil comprises at least 90% w/w capsaicin.

15. The oil of claim 1 wherein the capsaicinoid is capsaicin and wherein the oil comprises at least 95% w/w capsaicin.

16. The oil of claim 1 where the capsaicinoid is capsaicin.

17. A method of treating a capsaicinoid-responsive condition in a subject comprising administering the oil of claim 1.

18. The method of claim 17 wherein the oil is applied topically to the skin or a mucous membrane of the subject.

19. The method of claim 18 wherein the oil is applied for at least about 10 minutes.

20. The method of claim 18 wherein the oil is applied for at least about 30 minutes.

21. The method of claim 18 wherein the oil is applied for at least about one hour.

22. The method of claim 18 further comprising removing the oil with a cleansing gel.

23. A method for making a topical oil in unit dosage form comprising the steps of:
solubilizing at least 40% w/w capsaicin in a volatile or semi-volatile solvent;
adding a capsaicin crystallization inhibitor; and
removing substantially all of the volatile or non-volatile solvent, wherein the oil is stable at room temperature.

24. The method of claim 23 wherein the capsaicin crystallization inhibitor is polyvinylpyrrolidone.

25. The method of claim 23 wherein the solvent is a volatile solvent selected from the group consisting of ethanol, isopropyl alcohol, and mixtures thereof.

26. The method of claim 23 wherein the solvent is a semi-volatile solvent selected from the group consisting of terpenes, tea tree oils, essential oils, and mixtures thereof.

* * * * *